US00PP35868P2

(12) United States Plant Patent
Geibel

(10) Patent No.: US PP35,868 P2
(45) Date of Patent: Jun. 11, 2024

(54) ***PELARGONIUM* PLANT NAMED 'PACPX15505'**

(50) Latin Name: ***Pelargonium zonale* x *P. peltatum* interspecific hybrid**
Varietal Denomination: PacPX15505

(71) Applicant: Elsner Pac Jungpflanzen GbR, Thiendorf (DE)

(72) Inventor: Martin Geibel, Dresden (DE)

(73) Assignee: Elsner Pac Jungpflanzen GbR, Thiendorf (DE)

( * ) Notice: Subject to any disclaimer, the term of this patent is extended or adjusted under 35 U.S.C. 154(b) by 0 days.

(21) Appl. No.: 18/369,469

(22) Filed: Sep. 18, 2023

(51) Int. Cl.
*A01H 5/02* (2018.01)
*A01H 6/42* (2018.01)

(52) U.S. Cl.
USPC ..... Plt./329

(58) Field of Classification Search
USPC ..... Plt./324, 325, 329
See application file for complete search history.

*Primary Examiner* — Susan McCormick Ewoldt
*Assistant Examiner* — Zachariah Allan Kay
(74) *Attorney, Agent, or Firm* — The Webb Law Firm

(57) ABSTRACT

A new and distinct *Pelargonium* plant having single, pink flowers with a large, red eye and a compact habit.

1 Drawing Sheet

Botanical classification: *Pelargonium zonale* x *P. peltatum* interspecific hybrid.
Varietal denomination: 'PacPX15505'.

BACKGROUND OF THE INVENTION

The present invention comprises a new and distinct *Pelargonium* variety having the varietal name 'PacPX15505' and a botanical classification of *Pelargonium zonale* x *P. peltatum* interspecific hybrid. The new variety was discovered and selected in a planned breeding program in Dresden, Germany in the spring of 2015. The purpose of the breeding program was to develop interspecific *Pelargoniums* with bicolored flowers and moderate growth. The new variety is the result of crossing a bulk of different genotypes in the summer of 2014 in Dresden, Germany to obtain the applied-for variety. As such, the true parentage is unknown. The new variety was first asexually reproduced in January of 2016 by cuttings in Dresden, Germany. The new variety has been trial and field tested and has been found to retain its distinctive characteristics and remain true to type through successive propagations.

The new variety is similar to 'Pactiopisl' (U.S. Plant Pat. No. 33,316) in having a mounded plant shape and basal branching with pink flowers. However, 'Pactiopisl' is more vigorous and has a less distinct flower pattern than the new variety. The following characteristics further distinguish the new variety from other *Pelargonium* varieties known to the breeder:

Early and high flowering;
Single, pink flowers with a large, red eye;
Compact and uniform growth habit.

DESCRIPTION OF THE DRAWING

The accompanying photographic drawing illustrates the new variety at approximately 4 months of age, with the color being as nearly true as is possible with color illustrations of this type.

DESCRIPTION OF THE PLANT

The following detailed description sets forth the characteristics of the new cultivar. The data which defines these characteristics was collected from asexual reproductions and carried out in a greenhouse from spring through fall in Thiendorf, Germany. The new variety was grown in a 19.0 cm pot, with treatment of Cycocel® 720 0.2% two times, and no pinching or photoperiodic treatments. The average day temperatures were 18° C. and the average night temperatures were 16° C. The readings and measurements were taken on plants at approximately 8-9 months of age under a light level of 15-100 klux. Color references are primarily to the 1995 edition of the R.H.S. Colour Chart of The Royal Horticultural Society of London, except where terms of ordinary color significance are used.

PLANT

Time to initiate roots (days, temperature): From 18-22 days at about 18-20° C.
Time to develop roots (days, temperature): About 28 days at about 18-20° C.
Time to produce a finished flowering plant from a rooted cutting: About 75 days in a 13 cm container.
Type: Potted annual. Possibly a perennial in frost-free environments.
Root description: Dense, thin, fibrous, white, and freely branching.
Form: Mounded.
Height from media surface to top of foliage: 20.0 cm.
Height from media surface to top of flowers: 25.0 cm.
Plant diameter: 50.0 cm.
Vigor: Moderate.
Branching:
*Type.*—Basal.
*Primary branches.*—10.
*Secondary branches per primary.*—5.
*Lateral branch length.*—15.0 cm.
*Lateral branch diameter.*—8.0 mm.
*Internode length.*—1.0 cm.
*Stem appearance.*—Rounded in diameter.
*Stem aspect angle.*—Narrow.
*Stem strength.*—Strong.

*Stem color.*—Developing: 146C. At internodes: 146C. Developed: 152A.
*Luster.*—Semi-glossy.
*Pubescence.*—Medium.

Foliage:
*Arrangement.*—Mainly opposite.
*Type.*—Single.
*Size of leaf.*—Length: 4.9 cm. Width: 7.7 cm.
*Shape of leaf* (*generally*).—Round.
*Shape of apex.*—Round.
*Shape of base.*—Wide open.
*Margin type.*—Shallow-lobed and crenate.
*Sinus orientation.*—Divergent.
*Texture.*—Leathery (both surfaces) with a slightly rough upper surface.
*Luster.*—Upper surface: Matte. Lower surface: Matte.
*Pubescence.*—Present (both surfaces).
*Color.*—Young leaves: Upper surface: 147A. Lower surface: 147B. Mature leaves: Upper surface: 147A. Lower surface: 147B.
*Veins.*—Venation type: Palmate. Color: Upper surface: 147A. Lower surface: 147B.
*Petiole.*—Length: 8.0 cm. Diameter: 2.0 mm. Texture: Rough. Luster: Semi-glossy. Strength: Medium. Color: 147B.
*Stipules.*—Length: 12.0 mm. Width: 10.0 mm. Texture: Pubescent. Color: 144A.

INFLORESCENCE

Bud:
*Shape.*—Elliptic.
*Length.*—12.0 mm.
*Width.*—5.0 mm.
*Texture.*—Pubescent.
*Luster.*—Matte.
*Color.*—144A.

Natural flowering season: April until frost in moderate climates.
Arrangement: Inflorescence; umbel.
Flower type and form: Zygomorphic; flat.
Inflorescence height: 5.0 cm.
Inflorescence diameter: 8.5 cm.
Aspect: Upright.
Flowering habit: Free.
Number of flowers per inflorescence: 22.
Average time to flowering: 75 days.
Longevity on the plant:
*Umbel.*—3-4 weeks.
*Single flower.*—6-10 days.
Persistent or self-cleaning: Persistent.
Floral bracts: Absent.

Flower:
*Shape.*—Round.
*Height.*—46.0 mm.
*Diameter.*—46.0 mm.
*Depth.*—15.0 mm.

Petals:
*Arrangement.*—Single.
*Number per flower.*—5.
*Number of whorls.*—1.
*Fused.*—No.
*Length.*—Upper petals: 26.0 mm. Lower petals: 25.0 mm.
*Width.*—Upper petals: 21.0 mm. Lower petals: 25.0 mm.
*Shape.*—Obovate.
*Apex shape.*—Round.
*Base shape.*—Pointed.
*Margin.*—Entire with low undulation.
*Texture.*—Smooth with no rugosity (both surfaces).
*Luster.*—Glossy (both surfaces).
*Upper surface color.*—When opening: 57D, with 45A marking. Fully opened: 57D, with 45A marking. Fading: 57D. Venation: 57D, with 57A at the base.
*Lower surface color.*—When opening: 62C. Fully opened: 62C. Fading: 62C. Venation: 62D.

Petaloids:
*Quantity.*—0-2 per flower and randomly distributed.
*Shape.*—Irregular.
*Number of whorls.*—1 and unfused.
*Length.*—Approximately 1.0 cm.
*Width.*—Approximately 5.0 mm.
*Apex.*—Pointed to round.
*Base.*—Pointed.
*Margin.*—Irregular with medium undulation.
*Texture.*—Smooth with no rugosity (both surfaces).
*Luster.*—Glossy (both surfaces).
*Upper surface color.*—When opening: 57C. Fully opened: 57C. Fading: 57C. Venation: 57C.
*Lower surface color.*—When opening: 62C. Fully opened: 62C. Fading: 62C. Venation: 62B.

Calyx:
*Shape.*—Round.
*Length.*—8.0 mm.
*Diameter.*—24.0 mm.
*Sepals.*—Arrangement: Radiate. Number per flower: 5. Number of whorls: 1. Spurs: Absent. Length: Upper sepals: 12.0 mm. Lower sepals: 12.0 mm. Width: Upper sepals: 4.0 mm. Lower sepals: 2.0 mm. Shape: Lanceolate and unfused. Apex: Pointed. Base: Broad. Margin: Entire. Upper surface texture: Smooth. Lower surface texture: Pubescent. Luster: Glossy (both surfaces). Upper surface color (opening and opened): 144A. Lower surface color (opening and opened): 144A.

Peduncle:
*Length.*—12.0 cm.
*Diameter.*—4.0 mm.
*Aspect.*—Upright angle from lateral branch axis.
*Strength.*—Strong.
*Texture.*—Pubescent.
*Luster.*—Semi-glossy.
*Color.*—144A.

Pedicel:
*Length.*—27.0 mm.
*Diameter.*—1.0 mm.
*Aspect.*—Narrow angle from peduncle axis.
*Strength.*—Elastic.
*Texture.*—Pubescent.
*Luster.*—Semi-glossy.
*Color.*—144A and 166B.

Fragrance: None.
Keeping quality: 20 days.
Disease/pest resistance: Unknown.

Temperature tolerance: From 0-40° C.
Drought/rain/wind tolerance: Moderate.
Fruit/seed: None observed.

REPRODUCTIVE ORGANS

Stamen:

*Number* (*per flower*).—9.
*Filament.*—Length: 5.0 mm. Color: White.
*Anther.*—Shape: Short tube. Length: 2.0 mm. Width: 1.0 mm. Color: 57B.
*Pollen.*—Color: 167A. Amount: Abundant.

Pistil:

*Number.*—1.
*Length.*—7.0 mm.
*Style.*—Length: 2.0 mm. Color: 57A.
*Stigma.*—Shape: Actinomorphic, 5-parted. Diameter: 4.0 mm. Color: 57A.
*Ovary color.*—139D.

I claim:

1. A new and distinct variety of *Pelargonium* plant named 'PacPX15505', as is herein illustrated and described.

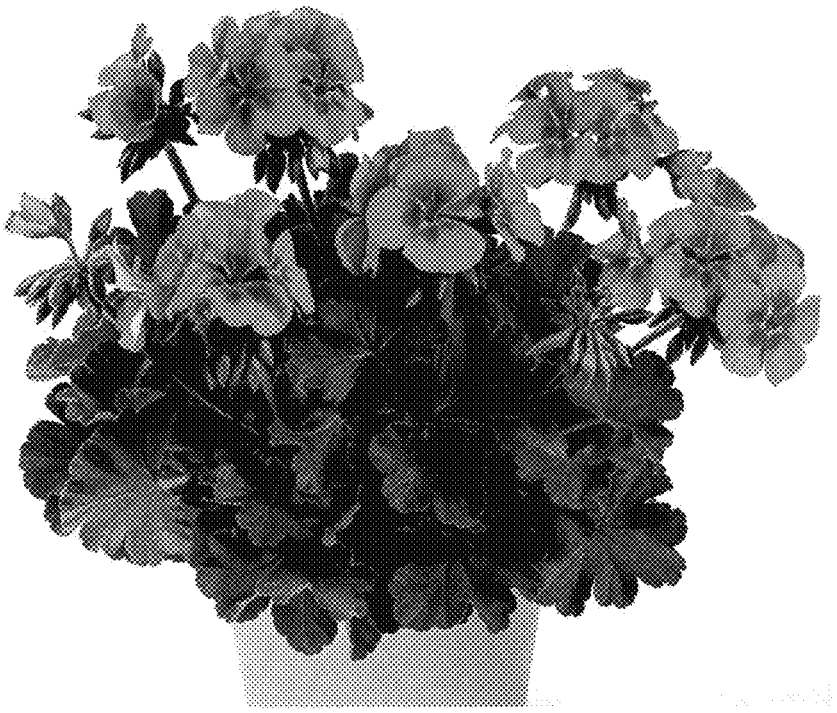

* * * * *